(12) United States Patent
Schmid et al.

(10) Patent No.: US 8,888,759 B2
(45) Date of Patent: Nov. 18, 2014

(54) MEDICAL DEVICE WITH HYDROPHILIC COATING

(75) Inventors: Andrea Schmid, Moelnlycke (SE); Marie Svensson, Gothenburg (SE)

(73) Assignee: Astra Tech AB, Molndal (SE)

( * ) Notice: Subject to any disclaimer, the term of this patent is extended or adjusted under 35 U.S.C. 154(b) by 344 days.

(21) Appl. No.: 12/425,701

(22) Filed: Apr. 17, 2009

(65) Prior Publication Data

US 2009/0264869 A1 Oct. 22, 2009

Related U.S. Application Data

(60) Provisional application No. 61/071,217, filed on Apr. 17, 2008.

(30) Foreign Application Priority Data

Apr. 17, 2008 (EP) .................... 08154718

(51) Int. Cl.
- A61M 1/00 (2006.01)
- A61M 25/00 (2006.01)
- A61L 29/08 (2006.01)

(52) U.S. Cl.
CPC ..... *A61M 25/0009* (2013.01); *A61M 2025/006* (2013.01); *A61M 2025/0046* (2013.01); *A61L 29/085* (2013.01)
USPC ........................................................ 604/540

(58) Field of Classification Search
USPC ............ 604/93.01, 540, 541, 544; 428/304.4, 428/306.6, 313.5
See application file for complete search history.

(56) References Cited

U.S. PATENT DOCUMENTS

| 4,373,009 A | 2/1983 | Winn |
| 5,331,027 A | 7/1994 | Whitbourne |
| 2004/0175558 A1 * | 9/2004 | El-Nounou et al. ....... 428/304.4 |
| 2004/0191442 A1 | 9/2004 | Lim |

FOREIGN PATENT DOCUMENTS

| WO | WO-97/29160 A1 | 8/1997 | |
| WO | WO-99/38546 A1 | 8/1999 | |
| WO | WO 9938546 A1 * | 8/1999 | ............. A61L 29/00 |
| WO | WO-00/61205 A1 | 10/2000 | |

OTHER PUBLICATIONS

XP009105876, ISO Standard 4287:1997, Apr. 1, 1997.

* cited by examiner

*Primary Examiner* — Melanie Hand
(74) *Attorney, Agent, or Firm* — Birch, Stewart, Kolasch & Birch, LLP

(57) ABSTRACT

A medical device is disclosed, comprising a substrate and a hydrophilic surface coating arranged on said substrate. The substrate has, on its surface coated with said hydrophilic surface coating, a surface texture with an arithmetical mean deviation of the surface profile (Ra) of at least 3 μm and/or a profile section height difference (Rdc (1-99%)) of at least 18 μm. It has surprisingly been found that the increased surface roughness of the substrate provides significant improvements in e.g. water retention for the hydrophilic coating.

21 Claims, No Drawings

MEDICAL DEVICE WITH HYDROPHILIC COATING

This Non-provisional application claims priority under 35 U.S.C. §119(e) on U.S. Provisional Application No. 61/071,217 filed on Apr. 17, 2008, and under 35 U.S.C. §119(a) on Patent Application No. 08154718.4 filed in European Patent Community on Apr. 17, 2008, the entire contents of all of the above applications are hereby incorporated by reference into the present application.

FIELD OF THE INVENTION

The present invention generally relates to medical devices which present a substrate, such as an elongate shaft, having an outer hydrophilic surface coating. In particular the invention relates to a catheter for insertion into a passageway in a human or animal body, and specifically urinary catheters. The invention is also related to a corresponding method of manufacture and use.

BACKGROUND OF THE INVENTION

Many medical devices incorporate elongate shafts such as tubes which are intended for insertion into and through passageways of a living body such as those of the urethral tract and the cardiovascular system. The most common type of this general grouping of medical devices are known as catheters. Exemplary catheters include those designated for urological, angioplasty and valvuloplasty uses, that is, adapted respectively for insertion into the urethra, the lumen of a blood vessel and heart passageway of a living body, normally a human body.

Because of the intended use of such medical devices certain parameters need to be satisfied by the material from which the elongate shaft is manufactured. The material must fulfill such requirements as softness, good kink resistance, good dimensional stability, processability, for example ease to form and glue, and the possibility to be sterilized by radiation, steam, ethylene oxide or other means. There is further the need for the material to accept a surface treatment which will impart desired surface properties to the medical device, such as hydrophilicity. To this latter end, it is of utmost importance to find a substrate material that enables the possibility to coat the substrate.

Further, a well-recognized problem with hydrophilic coatings or layers has been that the hydrophilic polymer surface may lose water and dry out when it comes in contact with e.g. a mucous membrane, such as when the catheter is inserted into the urethra. This occurs because of a difference between the osmotic potential of the hydrophilic surface and the osmotic potential of the mucous membrane. The mucous membrane has a higher osmotic potential, i.e. a higher salt concentration, than the hydrophilic surface. This difference in osmotic potential causes the water to go from the hydrophilic surface layer to the mucous membrane so that the difference in the salt concentration will be counter-balanced. Naturally, this affects the low-friction properties of the hydrophilic outer surface coating, and may lead to pain and injuries of the patient. For this reason, the present applicant has previously developed an improved hydrophilic coating, in which an osmolality-increasing compound was applied to a non-reactive hydrophilic polymer surface, thereby producing a more stable hydrophilic surface, as is disclosed in EP 217 771. Hereby, the theretofore prevailing problem of the hydrophilic coating drying out when inserted into the urethra, thus rendering the article insufficiently hydrophilic, was alleviated.

Similar hydrophilic coatings incorporating an osmolality-increasing compound are discussed in WO 94/16747 disclosing a process in which the osmolality-increasing compound is added during the process of applying the hydrophilic coating to the base material, EP 586 324 and EP 591 091 disclosing a hydrophilic coating comprising a non-dissolved, solid osmolality-increasing compound e.g. in the form of a powder or grain, and EP 991 702 disclosing a cross-linked hydrophilic coating comprising a water soluble osmolality-increasing compound.

However, these known methods and coatings are affected by some problems. For example, the production processes, involving different manners of incorporating the osmolality-increasing compounds in the coatings, are rather tedious cumbersome and costly. Further, the properties of the resulting, wetted hydrophilic surface coating to be inserted into the patient are, at least to a certain extent, affected by parameters of the wetting process, such as the quantity of wetting fluid used for the wetting, the constituents of the chosen wetting fluid, and the time period during which the wetting is carried through. Since several such parameters may be unknown beforehand, and may vary to a significant degree, the properties of the resulting, activated coating become unpredictable as well.

Thus, there is a general problem of known medical devices with hydrophilic coatings that water retention in the coating is too low, especially after leaching, or that the coating has too poor adherence to the substrate, and/or that the means used for prolonging the water retention time and the adherence of the coating is too costly and/or harmful to the environment.

There is therefore a need for an improved substrate and or coating method for providing medical devices with a hydrophilic surface coating, which is environmentally acceptable and cost effective, and which ensures that the hydrophilic coating can be adequately adhered and is efficient in use.

SUMMARY OF THE INVENTION

It is a general object of the present invention to alleviate the above-discussed problems. One particular object of the present invention is to provide a medical device, such as a urinary catheter, with a hydrophilic surface coating, where the water retention capability of the hydrophilic coating is improved. Other general and specific objects of the invention will in part be obvious and will in part appear hereinafter.

These objects are achieved with a medical device and a production method according to the appended claims.

According to a first aspect, there is provided a medical device comprising a substrate and a hydrophilic surface coating arranged on said substrate, wherein the substrate has, on its surface coated with said hydrophilic surface coating, a surface texture with an arithmetical mean deviation of the surface profile (Ra) of at least 3 µm and/or profile section height difference (Rdc (1-99%)) of at least 18 µm. Preferably, the surface texture fulfills both the Ra and Rdc (1-99%) criteria.

The arithmetical mean deviation of the surface profile (Ra) and the profile section height difference (Rdc (1-99%)) are, as used in this application, in correspondence with the definitions provided in ISO 4287:1997, with the title "Geometrical Product Specifications (GSP)—Surface texture: Profile method—Terms, definitions and surface texture parameters. This definition is also generally in line with the similar definitions provided in ISO 11562:1996 titled "Geometrical Product Specifications (GSP)—Surface texture: Profile method—Metrological characteristics of fase correct filters" and ISO 4288:1996 titled "Geometrical Product Specifications (GSP)—Surface texture: Profile method—Rules and procedures for the assessment of surface texture".

The present inventors have surprisingly found that the water retention of an hydrophilic surface coating is significantly improved when the hydrophilic coating is applied to a substrate with an increased surface texture or surface roughness. This may, at least partly, be due to an increased adherence to the substrate, which in turn may be due to increased exposure to bonding sites between the coating and the substrate. However, the present patent is not to be bound by any specific theory of the origin of the remarkable improvement being demonstrated by means of the present invention.

The coating applied on substrates in accordance with the present invention also adheres stronger to the substrate, thereby reducing the risk of the coating falling off or being significantly deteriorated during use. This effect is e.g. evident from the fact that similar improvements in water retention is experienced even after leaching of the coated substrate.

It has been noted that at least up to excessive levels, the improvement in water retention increases even further when the surface texture has an Ra which exceeds 4.0, and preferably exceeds 5.0. Similarly, the surface texture preferably has an Rdc (1-99%) which exceeds 20, and preferably exceeds 25. However, as a preferred upper limit, the surface texture has an Ra which is less than 20.0, and most preferably less than 15.0, and most preferably equal to or less than 10.0. Similarly, the surface texture preferably has an Rdc (1-99%) which is less than 75, and preferably less than 60, and most preferably equal to or less than 50.

Even though it is expected that similar positive effects are present in many types of substrate materials, it has been demonstrated that the effect is particularly pronounced in substrates made of a plastic material, and in particular when the substrate comprises a material selected from the group consisting of: polyether block amid, poly vinyl chloride (PVC), and polypropene, polyethen polyamide and styrenethen/buten-styren co-polymer.

Similarly, it has been found by the present invention that the improvement is particularly noticeable for hydrophilic coatings comprising polyvinylpyrrolidone.

According to another aspect of the present invention, there is provided method of producing a medical device with a hydrophilic surface coating, comprising the steps of:

providing a substrate material having a surface texture with an arithmetical mean deviation of the surface profile (Ra) of at least 3 μm and/or a profile section height difference (Rdc (1-99%)) of at least 18 μm;

coating said substrate material with a hydrophilic surface coating.

According to this aspect of the invention, similar advantages as discussed above in relation to the first aspect of the invention are at hand.

Preferably, both the Ra and Rdc (1-99%) criteria are fulfilled by the surface texture of the substrate material.

The hydrophilic coating preferably forms a polyurea network, whereby said polyurea network forms a covalent bond to said active hydrogen groups in the substrate. Alternatively, the hydrophilic coating may form an ester bond or an epoxy bond to said active hydrogen groups in the substrate.

The step of coating the substrate material preferably comprises the sub-steps of: applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature.

However, other hydrophilic coatings are also feasible, such as a coating comprising hydrophilic polymers cross-linked directly to the substrate. The cross-linking may be effected by means of irradiation, e.g. by electron beams or UV light.

These and other aspects of the inventive concept will be apparent from and elicited with reference to the embodiments described hereinafter.

DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. The hydrophilic catheters may be used for many different purposes, and for insertion into various types of body-cavities. However, the following discussion is in particular concerned with the preferred field of use, urinary catheters, even though the invention is not limited to this particular type of catheters. However, it is to be appreciated by those skilled in the art that the inventive concept is not limited to this type of devices, but could also be used in many other types of medical devices.

A urinary catheter normally comprises a drainage end, often provided with a flared rearward portion, and an elongate shaft or tube projecting forwardly from the rearward portion. An open-ended internal lumen extends from the rear end of the rearward portion to a drainage aperture in a rounded tip of the elongate tube. The rearward portion may function as a connector of the catheter, being connectable to other devices, such as a urine collection bag, a drainage tube or the like.

At least a part of the elongate tube forms an insertable length to be inserted through a body opening of the user, such as the urethra in case of a urinary catheter. By insertable length is normally, in the context of a hydrophilic catheter, meant that length of the elongate tube which is coated with a hydrophilic material, for example PVP, and which is insertable into the urethra of the patient. Typically, this will be 80-140 mm for a female patient and 200-350 mm for a male patient.

The elongate shaft/tube of the catheter is made of a substrate material. The substrates may be made from any polymer material, which are well-known in the technical field and to which the said hydrophilic polymers adhere, such as polyurethanes, latex rubbers, other rubbers, polyvinylchloride, other vinyl polymers, polyesters and polyacrylates. However, preferably the substrate is made of a polymer blend comprising a polyolefin and a composition having molecules with active hydrogen groups, and preferably a composition having molecules with active hydrogen groups. The polyolefin can comprise at least one polymer selected from the group: polyethene, polypropene, and styrene block copolymer (SCBS). The composition having molecules with active hydrogen groups can be a polymer having active hydrogen groups bound to the polymer via nitrogen, such as polyamide or polyurethane.

The hydrophilic coating is arranged on at least part of the substrate forming the catheter shaft. The hydrophilic polymer coating may comprise material selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone.

The coating may also comprise an osmolality-increasing compound, as is e.g. taught in EP 0 217 771.

The substrate is further provided with a pronounced surface texture or surface roughness on its surface to be covered by the hydrophilic coating. Such a pronounced surface roughness/texture is easily producible by adequately controlling the extrusion process during manufacture of the substrate shafts. Specifically, in extrusion equipment having various temperature zones, it is often possible to increase the surface roughness by increasing the temperature in the early stages of the extrusion process, and by lowering the temperature at the later stages, or by making an overall lowering of the temperatures. However, the temperature settings required for obtaining an adequate surface texture differs between different materials, and also varies significantly between different extrusion equipment, as would be known by any one of ordinary skill in the art. Alternatively or additionally, it is also possible to obtain an adequate surface texture by a surface treatment after extrusion, such as by mechanical roughening of the surface, chemical etching, plasma surface treatment, e.g. plasma deposition, electron-beam technology, ion beam sputter texturing, etching, e.g. ion etching, microwave radiation, sputtering, sintering, grinding, polishing, milling, photolithography, laser treatment, microblasting etc.

The surface texture is produced to have at least one, and preferably both, of a surface profile (Ra) equal to or exceeding 3 μm and a profile section height difference (Rdc (1-99%)) equal to or exceeding 18 μm. Preferably, Ra exceeds 4.0, and preferably exceeds 5.0. Similarly, the surface texture preferably has an Rdc (1-99%) which exceeds 20, and preferably exceeds 25. However, as a preferred upper limit, the surface texture has an Ra which is less than 20.0, and most preferably less than 15.0, and most preferably equal to or less than 10.0. Similarly, the surface texture preferably has an Rdc (1-99%) which is less than 75, and preferably less than 60, and most preferably equal to or less than 50.

The present inventors have surprisingly found that the water retention of an hydrophilic surface coating is significantly improved when the hydrophilic coating is applied to a substrate with such an increased surface texture or surface roughness.

Some preferred examples of methods for applying a hydrophilic surface coating to the substrate will now be discussed in greater detail. However, it is to be noted that the above-discussed substrate material having an increased surface roughness can also be used for many other coating methods for obtaining an improved hydrophilic surface coating.

A preferred method for coating of the substrate will now be disclosed in more detail. The outer surface of the elongate shaft is preferably coated with a stable hydrophilic coating by applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature. The isocyanate solution may advantageously contain between 0.5 to 10% (weight to volume) of the isocyanate compound, and may preferably contain between 1 to 6% (weight to volume) of the isocyanate compound. Generally, the isocyanate solution only needs to be in contact with the surface briefly, for example 5 to 60 sec.

Application of the isocyanate solution to the substrate surface results in a coating having unreacted isocyanate groups being formed on the substrate surface. Application of the polyvinylpyrrolidone solution to the substrate surface then results in a hydrophilic polyvinylpyrrolidone-polyurea interpolymer coating being formed. Curing of this hydrophilic coating binds the isocyanate compounds together to form a stable non-reactive network that binds the hydrophilic polyvinylpyrrolidone. To advantage, curing takes place in the presence of a water-containing gas, for example ambient air, to enable the isocyanate groups to react with the water to yield an amine which rapidly reacts with other isocyanate groups to form a urea cross-link. Further, the method may comprise the steps of evaporating the solvent of the isocyanate solution prior to application of the polyvinylpyrrolidone solution and evaporating the solvent of the polyvinylpyrrolidone solution prior to curing of the hydrophilic coating. This may for example be done by air drying.

The isocyanate compound preferably comprises at least two unreacted isocyanate groups per molecule. The isocyanate may be selected from 2,4-toluene diisocyanate and 4,4'-diphenylmethane diisocyanate, or a pentamer of hexamethylene diisocyanate and toluene diisocyanate of cyanurate type, or trimerized hexamethylene diisocyanate biuret or mixtures thereof.

The solvent for the isocyanate compound is preferably one which does not react with isocyanate groups. The preferred solvent is methylene chloride but it is also possible to use ethyl acetate, acetone, chloroform, methyl ethyl ketone and ethylene dichloride, for example.

In order to shorten the necessary reaction times and curing times suitable catalysts for isocyanate curing may be added. These catalysts may be dissolved in either the isocyanate solution or the polyvinylpyrrolidone solution but are preferably dissolved in the latter. Different types of amines are especially useful, for example diamines, but also for example triethylenediamine. Preferably, an aliphatic amine is employed which is volatisable at the drying and curing temperatures used for the coating, and which furthermore is non-toxic. Examples of suitable amines are N,N' diethylethylendiamine, hexamethylendiamine, ethylendiarnine, paradiaminobenzene, 1,3-propandiol-para-aminobenzoic acid diester and diaminobicyclo-octane.

The polyvinylpyrrolidone used preferably has a mean molecular weight of between $10^4$ to $10^7$ with the most preferred mean molecular weight being about $10^5$. Polyvinylpyrrolidone having such a molecular weight is commercially available, for example under the trademark Kollidon® (BASF). Examples of suitable solvents for polyvinylpyrrolidone that may be used are methylene chloride (preferred), ethyl acetate, acetone, chloroform, methyl ethyl ketone and ethylene dichloride. The proportion of polyvinylpyrrolidone in the solution is preferably between 0.5 to 10% (weight to volume) and most preferred between 2 to 8% (weight to volume). The polyvinylpyrrolidone in the solvent is applied by dipping, spraying or the like for a short period of time, e.g. during 5 to 50 sec.

Curing of the coating is preferably performed at a temperature of 50 to 130 deg. C., in for example an oven, for a duration of between 5 to 300 min.

In a preferred embodiment the hydrophilic coating contains an osmolality-increasing compound, for instance an inorganic salt selected from sodium and potassium chlorides, iodides, citrates and benzoates. The osmolality-increasing compound may be applied in the manner detailed in EP 0 217 771 by the same applicant.

Experiments

In experimental tests, substrates made of the following substrate materials were used:

Ex A: Polyether block amid (Pebax)

Ex A': Polyether block amid (Pebax)

Ex B: Poly vinyl chloride (PVC)
Ex B': Poly vinyl chloride (PVC)
Ex C: A combination of the materials Polypropene, Polyethen Polyamide and Styren-ethen/buten-styren co-polymer, sold under the trade name Meliflex
Ex C': Meliflex The materials of Ex A and Ex A' are identical, and the only difference between the substrates is that Ex A is extruded in such a way that it has an increased surface roughness compared to Ex A'. Correspondingly, the materials of Ex B and B' and Ex C and C', respectively, are also identical, the only difference residing in the surface roughness.

The substrates were coated with identical hydrophilic coating, in accordance with the method discussed above. Consequently, the catheters were prepared by dipping the substrates in a primer solution comprising a diisocyanate (named Desmodur IL), which is dissolved in methylene chloride to a concentration of 2% (weight/volume), for 15 seconds. The catheters were thereafter dried at ambient temperature for 60 seconds, and are then dipped for 3 seconds in a solution containing 6% (weight/volume) of polyvinylpyrrolidone (PVP K90) dissolved in methylene chloride. The catheters were then allowed to flush off at 35 deg. C. for 30 minutes, and then cured for 60 minutes at 80 deg. C., and were finally allowed to cool to room temperature and rinsed in water.

Further, an osmolality increasing compound, here NaCl, was subsequently added in accordance with the process described in EP 0 217 771.

For all the substrates, two measures of the surface roughness were measured:

The surface profile Ra [μm], providing a measure of the average height in μm over the base surface.

The profile section height difference Rdc (1-99%) [μm] providing a measure of the vertical distance between two section lines, said section lines being arranged at heights being covered by 1.0% and 99.0% of material, respectively.

Ra and Rdc were measured by means of a Hommel Tester T1000 Wave profilometer.

The water retention of the catheters, each pair differing only in the surface roughness of the substrates being used, were then tested for water retention in ambient air. To this end, the catheters were wetted during 30 sec., and the water content (mg/cm$^2$) in the hydrophilic coating was determined after 6 minutes. The water content was determined by weighing the catheters before wetting, to obtain a reference weight, and to measure the catheters a certain time after wetting, and subtracting the reference weight from this measurement. The obtained weight difference is a measure on the water content being held by the hydrophilic coating at the time of measurement.

The results of the surface texture measurements and the water retention measurements are presented in Table 1 below.

TABLE 1

Surface roughness of substrates and water retention [mg/cm$^2$] in coating

| Example | Material | Water retention after 6 minutes [mg/cm2] | Ra [μm] | Rdc [μm] |
|---|---|---|---|---|
| Ex A | Pebax | 8.97 (+/−0.39) | 5.80 (+/−0.70) | 33.14 (+/−3.69) |
| Ex A' | Pebax | 7.59 (+/−0.24) | 0.15 (+/−0.03) | 0.88 (+/−0.20) |
| Ex B | PVC | 5.14 (+/−0.39) | 7.14 (+/−0.82) | 41.99 (+/−4.36) |
| Ex B' | PVC | 3.85 (+/−0.32) | 0.85 (+/−0.31) | 5.19 (+/−1.81) |
| Ex C | Meliflex | 5.50 (+/−0.22) | 3.27 (+/−0.32) | 18.88 (+/−2.03) |
| Ex C' | Meliflex | 4.62 (+/−0.21) | 1.04 (+/−0.18) | 5.79 (+/−1.13) |

The above-discussed measurement data is mean values of a number of measurement, and the standard deviation is added within parentheses. Thus, the differences discussed in the following are statistically reliable, i.e. The standard deviation is significantly smaller than the deduced difference.

From this table it is clearly deducible that Ex A has a significantly improved water retention over Ex A' (Ex A: 8.97 mg/cm2 and Ex A': 7.59 mg/cm2), Ex B has a significantly improved water retention over Ex B' (Ex B: 5.14 mg/cm2 and Ex B': 3.85 mg/cm2), and Ex C has a significantly improved water retention over Ex C' (Ex C: 5.50 mg/cm2 and Ex C': 4.62 mg/cm2). These improvements is correlated with a significantly increased surface texture roughness, and thus with significantly higher values on Ra and Rdc, in Ex A compared to Ex A', in Ex B compared to Ex B' and in Ex C compared to Ex C'.

Based on the above-discussed experiments it is therefore fair to conclude that when using a substrate surface with increased roughness, in these examples with an Ra in the range 3-8 μm and an Rdc (1-99%) in the range 18-42, the water retention of the coating was significantly improved over identical substrates but with a smoother substrate surface, in these examples with an Ra in the range 0.5-1.5 μm and an Rdc (1-99%) in the range 0.5-6.

Similar improvements in water retention were also experienced in catheters subject to leaching for a certain time, such as for 6 minutes. This indicates that the coating on substrate surfaces with increased roughness also improves the adherence of the coating to the substrates.

In a further line of experiments, similar tests were made on hydrophilic catheters with a another type of hydrophilic coating. This hydrophilic coating was cross-linked to the substrate by means of UV-radiation.

As in the above-discussed examples, the materials of these Ex D and Ex D' are identical, and the only difference between the substrates is that Ex D is extruded in such a way that it has an increased surface roughness compared to Ex D'. Further, the substrate material used in Ex D and D' are poly vinyl chloride (PVC), similar to the material of Ex B and B' discussed in the foregoing.

More specifically, catheters having a cross-linked hydrophilic PVP coating were prepared in by dipping PVC catheter substrates in a primer solution comprising 4.9 parts of Plasdone K 90 (PVP K 90) and 0.1 parts of the photo initiator ESACURE KIP 150 dissolved in 95 parts of an ethanol/gamma butyrolactone (85/15) solvent mixture. The catheters were dipped in the primer solution with a speed of 20 mm/s, providing an average dipping time of about 20 sec. Subsequently, the catheters were dried for 1 minute at room temperature (20 deg. C.).

Thereafter, the catheters were dipped in a solution of 4 parts of Plasdone K90 (PVP K 90) dissolved in 96 parts of an ethanol/gamma butyrolactone (85/15) solvent mixture with a speed of 20 mm/s, providing an average dipping time of about 20 sec. The catheters were then dried for 30 minutes at 70 deg. C. After drying for 30 minutes, the PVC-catheters were exposed to UV-light for 150 sec. The UV source used emits light at a wavelength of 254 nm These catheters of Ex D and D' were, as in the previously discussed examples, tested in respect of surface profile Ra and profile section height difference Rdc (1-99%) [μm] by means of a Hommel Tester T1000 Wave profilometer. Further, the water retention of the catheters were tested for water retention in ambient air, in the same way as discussed above.

The results of the surface texture measurements and the water retention measurements are presented in Table 2 below.

TABLE 2

Surface roughness of substrates and water retention [mg/cm²] in coating

| Example | Material | Water retention after 6 minutes [mg/cm2] | Ra [µm] | Rdc [µm] |
|---|---|---|---|---|
| Ex D | PVC | 13.07 (+/−0.18) | 7.79 (+/−1.76) | 45.88 (+/−9.97) |
| Ex D' | PVC | 12.62 (+/−0.26) | 0.18 (+/−0.03) | 1.11 (+/−0.29) |

The above-discussed measurement data is mean values of a number of measurement, and the standard deviation is added within parentheses. Thus, the differences discussed in the following are statistically reliable, i.e. The standard deviation is significantly smaller than the deduced difference.

From this table it is clearly deducible that Ex D has a significantly improved water retention over Ex D' (Ex D: 13.07 mg/cm2 and Ex D': 12.62 mg/cm2). This improvement is correlated with a significantly increased surface texture roughness, and thus with significantly higher values on Ra and Rdc (1-99%), in Ex D compared to Ex D'.

Based on the above-discussed experiments it is therefore fair to conclude that this improvement, as discussed above in relation to Tables 1 and 2, is not dependent on any particular substrate material, and also not dependent on any particular type of hydrophilic coating. On the contrary, the above-discussed experiments show that the improvement is clearly obtainable in several different substrate materials, and for different types of hydrophilic coatings.

CONCLUSION AND SUMMARY

The invention has now been discussed in relation to different embodiments. However, it should be appreciated by those versed in the art that several further alternatives are possible. For example, the features of the different embodiments discussed above may naturally be combined in many other ways.

It is further possible to use the invention for other types of catheters than urinary catheters, such as vascular catheters or the like. It is also possible to use many different types of hydrophilic coatings. Many different materials could also be used for the different parts of the catheter assembly.

It will be appreciated by those versed in the art that several such alternatives similar to those described above could be used without departing from the spirit of the invention, and all such modifications should be regarded as a part of the present invention, as defined in the appended claims.

The invention claimed is:

1. A medical device comprising a substrate having a surface and a hydrophilic surface coating arranged on said surface of the substrate, wherein the surface of the substrate, underlying said hydrophilic surface coating, has a surface texture with at least one of the following:
an arithmetical mean deviation of the surface profile (Ra) according to ISO 4287:1997 of at least 3 µm; and
a profile section height difference (Rdc (1-99%)) according to ISO 4287:1997 of at least 18 µm,
wherein the substrate is made of a plastic material selected from the group consisting of: polyether block amid, poly vinyl chloride (PVC), and polypropene, polyethen polyamide and styren-ethen/buten-styren co-polymer.

2. The medical device of claim 1, wherein said surface texture has an arithmetical mean deviation of the surface profile (Ra) according to ISO 4287:1997 of at least 3 µm and a profile section height difference (Rdc (1-99%)) according to ISO 4287:1997 of at least 18 µm.

3. The medical device of claim 1, wherein said surface texture has an Ra according to ISO 4287:1997 of at least 4.0 µm.

4. The medical device of claim 1, wherein said surface texture has an Ra according to ISO 4287:1997 less than 20.0 µm.

5. The medical device of claim 1, wherein said surface texture has an Rdc (1-99%) according to ISO 4287:1997 of at least 20 µm.

6. The medical device of claim 1, wherein said surface texture has an Rdc (1-99%) according to ISO 4287:1997 less than 75 µm.

7. The medical device of claim 1, wherein the hydrophilic coating comprises polyvinylpyrrolidone.

8. A method of producing a medical device with a hydrophilic surface coating, comprising the steps of:
providing a substrate material having a surface texture with at least one of the following:
an arithmetical mean deviation of the surface profile (Ra) according to ISO 4287:1997 of at least 3 µm; and
a profile section height difference (Rdc (1-99%)) according to ISO 4287:1997 of at least 18 µm; and
coating said substrate material with a hydrophilic surface coating,
wherein the hydrophilic coating forms a polyurea network, whereby said polyurea network forms a covalent bond to active hydrogen groups in the substrate.

9. The method of claim 8, wherein the step of coating the substrate material comprises the sub-steps of: applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature.

10. The medical device of claim 1, wherein said surface texture has an Ra according to ISO 4287:1997 of at least 5.0 µm.

11. The medical device of claim 1, wherein said surface texture has an Ra according to ISO 4287:1997 less than 15.0 µm.

12. The medical device of claim 1, wherein said surface texture has an Ra according to ISO 4287:1997 equal to or less than 10.0 µm.

13. The medical device of claim 1, wherein said surface texture has an Rdc (1-99%) according to ISO 4287:1997 of at least 25 µm.

14. The medical device of claim 1, wherein said surface texture has an Rdc (1-99%) according to ISO 4287:1997 less than less than 60 µm.

15. The medical device of claim 1, wherein said surface texture has an Rdc (1-99%) according to ISO 4287:1997 equal to or less than 50 µm.

16. The medical device of claim 1, wherein the substrate comprises:
a material selected from the group consisting of:
poly vinyl chloride (PVC);
polyether block amid;
a combination of polypropene, polyethen, polyamide and styrene-ethen/buten-styren co-polymer;
polyesters;
polyacrylates; and
a polymer blend comprising polyolefin, and
a composition having molecules with active hydrogen groups, such as polyamide or polyurethane.

17. The medical device of claim 1, wherein the medical device is a urinary catheter, said catheter having an elongate tube forming an insertable length to be inserted through a body opening of the user, said elongated tube forming said substrate, and wherein the entire insertable length is coated with said hydrophilic surface coating.

18. The medical device of claim 16, wherein the polyolefin comprises at least one polymer selected from the group of polyethene, polypropene, and styrene block copolymer (SCBS).

19. A method of producing a medical device with a hydrophilic surface coating, comprising the steps of:
  providing a substrate material having a surface texture with at least one of the following:
    an arithmetical mean deviation of the surface profile (Ra) according to ISO 4287:1997 of at least 3 µm; and
    a profile section height difference (Rdc (1-99%)) according to ISO 4287:1997 of at least 18 µm; and
  coating said substrate material with a hydrophilic surface coating,
  wherein the step of coating the substrate material comprises the sub-steps of: applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature.

20. A medical device comprising a substrate having a surface and a hydrophilic surface coating arranged on said surface of the substrate, wherein the surface of the substrate, underlying said hydrophilic surface coating, has a surface texture with at least one of the following:
  an arithmetical mean deviation of the surface profile (Ra) according to ISO 4287:1997 of at least 3 µm; and
  a profile section height difference (Rdc (1-99%)) according to ISO 4287:1997 of at least 18 µm,
  wherein the substrate comprises:
  a material selected from the group consisting of:
    poly vinyl chloride (PVC);
    polyether block amid;
    a combination of polypropene, polyethen, polyamide and styrene-ethen/buten-styren co-polymer;
    polyesters;
    polyacrylates; and
    a polymer blend comprising polyolefin, and
  a composition having molecules with active hydrogen groups, such as polyamide or polyurethane.

21. The medical device of claim 20, wherein the polyolefin comprises at least one polymer selected from the group of polyethene, polypropene, and styrene block copolymer (SCBS).

* * * * *